United States Patent [19]

Burzynski

[11] Patent Number: 5,244,922
[45] Date of Patent: Sep. 14, 1993

[54] METHODS FOR TREATING VIRAL INFECTIONS

[76] Inventor: Stanislaw R. Burzynski, 20 W. Rivercrest, Houston, Tex. 77042

[21] Appl. No.: 888,976

[22] Filed: May 27, 1992

Related U.S. Application Data

[60] Continuation-in-part of Ser. No. 790,584, Nov. 8, 1991, which is a division of Ser. No. 577,464, Sep. 4, 1990, Pat. No. 5,089,508.

[51] Int. Cl.$^5$ ............................................ A61K 31/195
[52] U.S. Cl. .................................. 514/561; 514/563; 514/568
[58] Field of Search ...................... 514/561, 563, 568

[56] References Cited

U.S. PATENT DOCUMENTS

| | | | |
|---|---|---|---|
| 4,427,684 | 1/1984 | Ores | 514/328 |
| 4,558,057 | 12/1985 | Burzynski | 514/328 |
| 4,705,796 | 11/1987 | Hendry et al. | 514/328 |
| 4,835,151 | 5/1989 | Gittos | 514/219 |
| 4,940,705 | 7/1990 | Boshagene et al. | 514/227.8 |
| 5,110,600 | 5/1992 | Green | 424/45 |

FOREIGN PATENT DOCUMENTS 2103089 2/1983 United Kingdom .

OTHER PUBLICATIONS

Hodson et al. 95 CA:42938d 1981.
Singh et al 92 CA:105823y 1979.
Kreutzberger et al 82 CA:3853j.
Van Loon 90 CA:183336q 1979.

(List continued on next page.)

*Primary Examiner*—Frederick E. Waddell
*Assistant Examiner*—Russell Travers
*Attorney, Agent, or Firm*—Arnold, White & Durkee

[57] ABSTRACT

The present invention provides methods for treating viral diseases in humans by administering to an afflicted host pharmaceutical compositions containing a therapeutically effective amount of a combination of

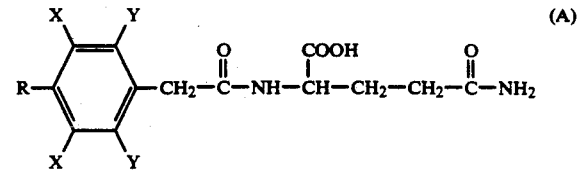

(A)

and

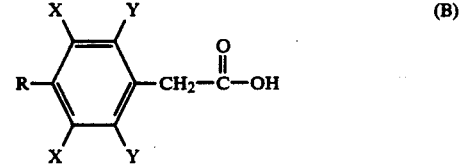

(B)

in a weight ratio ranging from about 1:1 to about 1:10 (A:B); wherein R is OH, NH$_2$, OW, or H; X is H, F, Cl, Br, I, OH, OW, NO$_2$, or NH$_2$; Y is H, F, Cl, Br, or I; W is

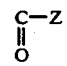

or a C$_1$ to C$_{12}$ aliphatic group;
Z is an aliphatic or aromatic group of C$_1$ to C$_{12}$;
X and Y can both vary within the compound; or pharmaceutically acceptable salts thereof.

Particularly disclosed herein is a composition comprising a 1 to 4 ratio of the sodium salts of phenylacetylglutamine and phenylacetic acid, formulated in both oral and parenteral forms clinically useful in the treatment of herpes virus, HIV, human papilloma virus, rhinovirus, coronavirus, orthomyxovirus and paramyxovirus.

19 Claims, No Drawings

OTHER PUBLICATIONS

Burzynski, S. R. et al., "Preclinical Studies on Antineoplaston AS2-1 and Antineoplaston AS2-5," CA 105:164561W (1986).

Ashraf, A. Q. et al., "Preclinical Studies on Antineoplaston A10 Injections," CA 105:164562X (1986).

Lehner, A. F. et al., "3-Phenylacetylamino-2,6-Piperidinedione, A Naturally-Occurring Peptide Analogue with Apparent Antineoplastic Activity, May Bind to DNA," Drugs Exptl. Clin. Res. Suppl. 1 12:57–72 (1986).

Burzynski, S., R. et al., "Purification, Structure Determination, Synthesis and Animal Toxicity Studies of Antineoplaston A10," 13th International Congress of Chemotherapy, pp. 1–11 (1983).

Burzynski, S. R., "Isolation, Purification, and Synthesis of Antineoplastons," International Journal of Experimental and Clinical Chemotherapy, pp. 63–69 (1989).

Laske et al., CA 112:111625H (1989).

Laske et al., CA 112:135860g (1989).

METHODS FOR TREATING VIRAL INFECTIONS

This application is a continuation-in-part of co-pending application Ser. No. 07/790,584, filed Nov. 8, 1991, which is a divisional application of application Ser. No. 07/577,464, filed Sep. 4, 1990, now issued as U.S. Pat. No. 5,089,508 on Feb. 18, 1992.

FIELD OF THE INVENTION

The present invention relates to the use of phenylacetyl derivatives in the treatment of viral diseases.

BACKGROUND OF THE INVENTION

Viruses are defined as minute infectious agents, not visible in the light microscope and unable to have independent metabolism and replicate outside the living cell. In order to multiply, viruses have to utilize living cell machinery. The living organism protects itself against viral infection by mounting nonspecific and specific (immune) defenses. The nonspecific mechanisms include phagocytosis, mechanical and chemical barriers, elevation of body temperature, inflammation and viral interference exerted by compounds such as interferons.

Phagocytosis in its primitive form is nonspecific, but it can be also viewed upon as a precursor of the immune defense. Until now phagocytosis seems to be the only defense of single cell organisms, such as protozoa against bacteria and viral infection. Whereas, it is undoubtedly successful as the defense mechanism of protozoa against bacteria, it is not sufficient to protect against viruses. Many different viruses will take advantage from being engulfed by phagocyte cells because this provides them an easy entry to the cell and they can then multiply in the phagocytes.

The obvious question to be asked is how unicellular organisms, such as protozoa, survived and were not eliminated by viruses over millions of years. It is postulated that protozoa possess a biochemical defense against viruses, which allows them to change the code governing reactions inside the cell and establish an environment hostile to virus replication. Two of such mechanisms have been found in protozoa already: deviation from the genetic code and RNA editing. According to data published by others, certain protozoa use stop codon TAG for incorporation of glutamine in the polypeptide chain (Preer, J. R. et al., Nature 314:188 (1985) and Caron, F. et al., Nature 314:185 (1988)). This allows the protein synthesis to continue through incorporation of glutamine instead of stopping at a stop codon. Such change will not allow viruses to produce correct proteins because the genetic code in viruses and protozoa will have different meaning.

RNA editing has been described in various protozoa and allows a change from cytosine to uracil in RNA (Powell, L. M. et al., Cell 50:831 (1987), Feagin, J. E. et al., Cell 53:413 (1988) and Simpson, L. et al., Cell 57:355 (1989)). This will result in stop codons UAG and UAA, instead of CAG and CAA, which are responsible for incorporation of glutamine. The outcome is production of different proteins than required by the viral genetic code.

As an additional response to viral infection, certain protozoa will multiply more rapidly and will form an entire colony instead of a single cell. Under such circumstances even if some cells die due to infection by the virus, the rest of the colony will survive.

To summarize, the defense of certain protozoa against viruses increases reliance on glutamine necessary for protein synthesis and stimulation of reproduction. The persistence of such mechanism in a higher organism may result in abnormal and uncontrolled cell growth leading to neoplastic growth.

As a possible defense mechanism, the multicellular organism can modify DNA bases. During the course of cellular differentiation, the tendency exists to eliminate methylated cytosine residues similar to the process of elimination of 5-methylcytosine in the course of evolution (Bird, A. P., Trends Genet. 3:342 (1987)). The final result is that cytosine is converted into thymine. This may decrease the rate of replication of DNA viruses which maintain CG base content higher than mature differentiated cells (Tooze, J., ed. The DNA Tumor Viruses, Molecular Biology of Tumor Viruses, 2d ed., Cold Spring Harbor, N.Y. 1981) and Baer, R. et al., Nature 310:207 (1984)). The disturbance of the differentiation process can delay modification of cytosine into thymine, create a greater reliance on glutamine because of persistence of CAG and CAA glutamine codons and allow the virus to replicate. Contrary to DNA viruses, the rate of evolutionary divergence of RNA viruses is very rapid which results in similar CG content in viral as well as host genome (Holland, J. et al., Science 215:1577 (1982) and Steinhauer, D. A. et al., J. Annu. Rev. Microbiol. 41:409 (1987)).

It is definitely advantageous for viruses to maintain host cells undifferentiated for as long as possible. Once the cell becomes terminally differentiated, the replication of certain viruses such as HIV, Herpes simplex and Epstein Barr virus may stop (Cullen, B. R. et al., Cell 58:423 (1989) and Garcia-Blanco, M. A. et al., Science 254:815 (1991)). On the other hand, undifferentiated cells require more glutamine. Induction of differentiation in the cells infected with virus, through inhibition of incorporation of glutamine may offer a chance to control the disease.

Without wishing to bound to any proposed theory, the present inventor postulates that the human body possesses a Biochemical Defense System (BDS) (Burzynski, S. R., Internat. J. Exp. Clin. Chemother. 2:63 (1989) and Burzynski, S. R., 17th Internat. Cong. Chemother., Berlin (1991)). This system parallels the immune defense, but protects the organism against the enemy within the body. The main purpose is no longer the defense against the micro-organism, but defense against defective cells. Such defective cells may occur as the result of viral infection. Chemical components of this biochemical defense system are peptides, amino acid derivatives and organic acids defined as antineoplastons (Burzynski, S. R., Physiol. Chem. Phys. 8:275 (1976) and Burzynski, S. R., U.S. Pat. No. 4,470,970). The mechanism of defense is based not on destruction, but on the reprogramming of defective cells through induction of differentiation.

The research on antineoplastons began in Poland in 1967 (Burzynski, S. R., Experientia 25:490 (1969) and Burzynski, S. R., Drugs Exptl. Clin. Res. Suppl. 1 12:1 (1986)). Initially, the work concentrated on the isolation of peptides which exist in the blood of healthy people and are deficient in cancer patients. Due to the small amount of raw material available for the study, in the following years, antineoplastons were isolated from urine instead of blood. In 1980 the structure of the first antineoplaston was identified and reproduced synthetically (Burzynski, S. R. et al., *Proc. 13th Internat. Cong. Chemother.*, Vienna, Austria 17, P.S. 12. 4. 11-4).

Antineoplastons are divided into two groups. One group contains compounds which have a wide spectrum of activity and includes Antineoplaston A1, A2, A3, A4, A5, A10, AS2-1, AS2-5. Antineoplastons A1, A2, A3, A4 and A5 contain peptides isolated from urine and Antineoplaston A10, AS2-1 and AS2-5 are the synthetic products. See e.g. U.S. Pat. Nos. 4,470,970, 4,558,057 and 4,559,325. In addition to the first group, there are antineoplastons that are active against a single specific type of neoplasm, such as Antineoplaston H, L and O. Antineoplaston A10 is the first active ingredient isolated and reproduced by synthesis. Acid hydrolysis of Antineoplaston A10 initially produces phenylacetyl-glutamine and phenylacetylisoglutamine. When hydrolysis is carried further, the products of reaction include phenylacetic acid, glutamic acid and ammonia. The sodium salt of phenylacetylglutamine was named Antineoplaston AS2-5 and the mixture of the sodium salts of phenylacetylglutamine and phenylacetic acid in the ratio of 1:4 was named Antineoplaston AS2-1 (AS2-1) (Burzynski, S. R. et al., *Drugs Exptl. Clin. Res. Suppl.* 1, 12:11 (1986)).

According to the present inventor, AS2-1 seems to induce differentiation by reducing the level of glutamine in cells and substituting glutamine with phenylacetylglutamine. Relative excess of glutamine is essential for entering S-phase of cell cycle (Zetterberg, A. et al., *Cell Physiol. Chem.* 108:365 (1981)). In Swiss 3T3 cells cultured and starved to quiescence, a relative excess of glutamine is necessary for approximately seven hours from the end of $G_o$ to the beginning of S phase (Zetterberg, A. et al., *Cell Physiol. Chem.* 108:365 (1981)).

The availability of glutamine for cells in the human organism is regulated through the well-known reaction of the conjugation of glutamine with phenylacetic acid to phenylacetylglutamine (Thierfelder, H. et al., *Z. Physiol. Chem.* 94:1 (1915)). Phenylacetic acid is produced in substantial amounts in the human body and over 90% is bound with glutamine to form phenylacetylglutamine (Seakins, J. W. T., *Clin. Chem. Acta.* 35:121 (1971)). The type of amino acid conjugated with phenylacetic acid is different for different animals and is correlated with their evolutionary status. Conjugation of glutamine seems to be specific for humans and old world monkeys (James, M. O. et al., *Proc. R. Soc. Lond. B.* 182:25 (1972)). Systemic administration of AS2-1 to a patient produces a relative deficiency of glutamine and introduces phenylacetyglutamine which competes with glutamine.

SUMMARY OF THE INVENTION

The present invention provides methods for treating viral infections in humans using a pharmaceutical composition containing a pharmaceutically acceptable carrier and a therapeutically effective amount of a combination of

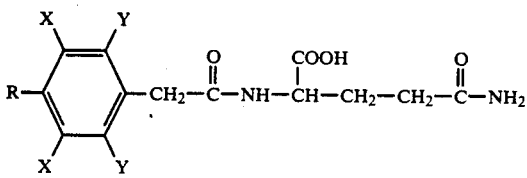

and

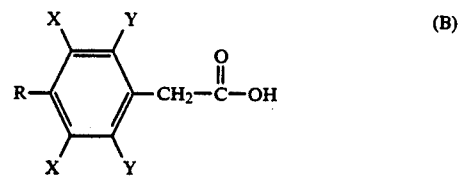

in a weight ratio ranging from about 1:1 to 1:10 (A:B); wherein R is OH, $NH_2$, OW, or H; X is H, F, Cl, Br, I, OH, OW, $NO_2$ or $NH_2$; Y is H, F, Cl, I or Br; W is

or a $C_1$ to $C_{12}$ aliphatic group;

Z is an aliphatic or aromatic group of from $C_1$ to $C_{12}$;

X and Y can both vary within the compound; or pharmaceutically acceptable salts thereof.

As used herein, "pharmaceutically acceptable salts" mean salts having the biological activity of the parent compound and lacking unusually toxic activity at the selected administration level. Such salts include inorganic sodium, potassium and ammonium salts, organic diethanolamine, cyclohexylamine, and amino acid salts.

The pharmaceutical compositions described above exhibit significant in vivo activity as antiviral agents. Both RNA and DNA viral infections in mammalian hosts are amenable to treatment with the specified combination of phenylacetylglutamine derivatives and phenylacetic acid derivatives. Examples of DNA viruses include herpes virus such as herpes simplex types 1 and 2, varicella-zoster virus, Epstein-Barr virus, cyomegalovirus; adenovirus; and papovavirus such as human papilloma virus. Examples of RNA viruses include those that cause the common cold and flu (rhinoviruses, coronaviruses, orthomyxoviruses and paramyxoviruses) and retroviruses including lentiviruses such as visna virus and HIV. Tumorogenic viruses are also affected by the antiviral compositions of this invention.

Depending on the nature of the infection and manner in which it manifests itself (e.g. systemically or locally as with skin lesions), the antiviral compositions can be administered by using conventional modes of administration, e.g., orally, topically, parenterally, and the like. The antiviral composition comprises a suitable pharmaceutically acceptable carrier and the combination of active phenylacetylglutamine and phenylacetate derivatives in an amount effective to suppress the replication of and/or abort the infective life cycle of virus causing the infection.

In treatments using the antiviral combination, an antivirally effective dosage regimen should be used. Generally, in the treatment of viral infections, a proper dosage regimen requires providing the medication over a period of time to achieve noticeable therapeutic effects. As used herein, the expression "antivirally effect amount" or "therapeutically effect amount," or dosage, or regimen means that amount, dosage or regimen which results in sufficient concentrations of the active ingredient combination at cellular sites of infection necessary to inhibit virus replication and/or abort the infective virus life cycle.

A particular combination of two compounds, termed herein Antineoplaston AS2-1 (1:4 ratio of sodium salt of phenylacetylglutamine and sodium salt of phenylacetic acid) is particularly preferred and has been administered to human patients for the purpose of treating viral infectious diseases in the form of 500 mg capsules and 100 mg/ml intravenous infusions.

DETAILED DESCRIPTION OF THE PREFERRED EMBODIMENTS

I. Methods of Preparing the Compounds

Desired R,X,Y substituted derivatives of phenylacetic acid can be purchased commercially or prepared synthetically by methods known to those skilled in the art according to well established rules of electrophilic and nucleophilic aromatic substitution. For example, 4-hydroxyphenylacetic acid, which is commercially available from Aldrich Chemical Company, Inc., can be nitrated with dilute $HNO_3$ to produce 4-hydroxy-3-nitrophenylacetic acid that is used as is in the next step of reaction. Alternatively, the nitro group in 4-hydroxy-3-nitrophenylacetic acid can be reduced to the corresponding amine and then reacted with sodium nitrite in acid to form the diazonium salt, that can be converted into a wide range of functional groups, including chloro, fluoro, bromo and hydroxyl. Phenylacetic acid can alternatively be nitrated in the 4-position to produce 4-nitrophenylacetic acid, that is used as is in the reaction or converted to the diazonium salt and derivatized. The nitro group can be reduced to the corresponding amino group as a final step of reaction by methods known to those skilled in the art, including catalytic hydrogenation.

The compounds of this invention can be prepared by condensation of the appropriate R,X,Y substituted phenylacetic acid derivative with L-glutamine to produce the corresponding R,X,Y substituted phenylacetylglutamine derivative. The condensation reaction can be facilitated by prior activation of the phenylacetic acid derivative with a reagent such as N-hydroxy-succinimide in the presence of DCC (N,N-dicyclohexylcarbodiimide), 2-mercaptothiazoline in the presence of DCC, or DCC alone. These reactions are described in more detail in Burzynski, *Drugs of the Future* 10(2):103 (1985).

II. Preparation of Pharmaceutical Compositions and Mode of Administration

As stated above, the combination of R,X,Y substituted phenylacetic acid and R,X,Y substituted phenylacetylglutamine of the present invention is useful in the treatment of viral diseases. Pharmaceutical compositions, including these active compounds, can be prepared as described below.

Mixtures of the active compounds, or pharmaceutically acceptable salts thereof, are included in the pharmaceutically acceptable carrier or diluent in an amount sufficient to exert a therapeutic effect without serious side effect. The combination of active materials can be administered by any appropriate route, for example, orally, parenterally, intravenously, intradermally, subcutaneously, intraperitoneally, or topically, in liquid or solid form.

The concentration of active compounds in the drug composition will depend upon absorption, inactivation, and excretion rates of the active compound as well as other factors known to those skilled in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The combination active ingredient may be administered at once, or may be divided into a number of smaller doses to be administered at varying intervals of time, e.g., 1 to 9 times daily, typically 4 times daily. For less advanced cases of viral infection, oral treatment is effective. Typically, the patient is given the antiviral combination, such as Antineoplaston AS2=1 capsules, from 2 to 10 g/day, or 40 mg/kg/24 h to 150 mg/kg/24 h, and preferably, 6 g/day or 85 mg/kg/24 h. For advanced cases of viral infection, treatment in the form of intravenous infusions is used. The dosages for the combination of sodium salt phenylacetylglutamine and sodium salt of phenylacetic acid are from 2.0 g to 60 g/day. When these inventive compositions are to be administered by the topical route, the concentration in the suspension medium can vary from 0.1 to 100 mg active ingredients/ml. A preferred concentration range lies between 0.5 and 50 mg active ingredients/ml.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, capsules, elixirs, suspensions, syrups or the like. Pharmaceutically compatible binding agents and/or adjuvant materials can be included as part of the composition.

Although not required, the combination of active ingredients may be provided in a composition that protects it from the acidic environment of the stomach. The composition can be orally administered in combination with an antacid formulation. The composition can also be administered in an enteric coating that maintains its integrity in the stomach and releases the active compounds in the intestine.

The active compounds can also be mixed with other active materials that do not impair the desired action, or with materials that supplement the desired action, including other antiviral agents such as interferon or AZT.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline, distilled sterile water, or phosphate buffered saline (PBS). For topical application, the antiviral combination can be placed in dimethyl sulfoxide (DMSO) or in the form of ointments, creams, salves and the like.

The following examples illustrate the present invention in further detail.

EXAMPLE 1

(Patient: GM)

The patient is a 34-year-old white male who complained of recurrent infections. The patient was practicing homosexual lifestyle. This patient was in reasonable health until January 1989 when he was found to be HIV positive. The symptoms of the disease he had since then were recurrent upper respiratory infections and Herpes zoster infection in January 1990. In August 1989, he began treatment with zidovudine. After initial improvement, his T4 cell count began to decrease (from 741/mm$^3$ on Dec. 12, 1989 to 608/mm$^3$ on Mar. 6, 1990 and 420/mm$^3$ on Apr. 23, 1990). T8 cell count, after initial decrease, continued to increase. His T8 cell count on Dec. 12, 1989 was 836/mm$^3$ and 969/mm$^3$ on Mar. 6, 1990 and 1420/mm$^3$ on Apr. 23, 1990. After initial increase, T4/T8 ratio began to decrease (0.88 on Dec. 12, 1989, 0.62 on Mar. 6, 1990 and 0.30 on Apr. 23, 1990).

The patient began treatment with Antineoplaston AS2-1, 500 mg capsules on Apr. 20, 1990 and was advised to take three capsules four times daily with meals (1.5 g four times daily). He did not suffer any side effects and was feeling well during the course of treatment. The follow-up evaluation on May 21, 1990 and May 29, 1990 revealed continuous increase of T4 cell count (420/mm$^3$ on Apr. 23, 1990, 450/mm$^3$ on May 21, 1990 and 480/mm$^3$ on May 29, 1990). T8 cell count continued to decrease (1420/mm$^3$ on Apr. 23, 1990, 1080/mm$^3$ on May 21, 1990, 848/mm$^3$ on May 29, 1990). T4/T8 ratio continues to increase (0.30 on Apr. 23, 1990, 0.42 on May 21, 1990, 0.56 on May 29, 1990). Normal values for T8 count are from 250/mm$^3$ to 750/mm$^3$ and T4/T8 ratio is more than 0.9. The continuous increase of T4 cell count, decrease of T8 cell count and increase of T4/T8 ratio indicates objective improvement.

During the treatment with Antineoplaston AS2-1, the patient continued to take zidovudine at the same dosages as before the treatment with Antineoplaston AS2-1. Since he had continuous worsening while taking zidovudine before, it is not expected that zidovudine was instrumental in obtaining objective improvement.

EXAMPLE 2

(Patient: LM)

The patient is a 29-year-old male who was complaining of shortness of breath, cough, night sweats, fever and loss of 25 pounds of weight within three weeks before coming under my treatment.

This patient was in good health until the beginning of April 1990 when he was diagnosed with Hodgkin's disease of mixed cellularity. The diagnosis was based upon the biopsy of the cervical lymph node. The patient was found to have enlargement of liver and spleen and multiple lymph nodes in the neck, chest and the abdomen. The bone marrow biopsy was highly suggestive of involvement with Hodgkin's disease. The laboratory test done at the beginning of the treatment for Hodgkin's disease indicated HIV infection which prompted the final diagnosis of Hodgkin's disease, stage IV associated with AIDS. The patient associated his HIV infection with intravenous use of narcotics. He did not receive any previous treatment for AIDS and Hodgkin's disease.

This patient began the treatment with Antineoplaston A10, 100 mg/ml intravenous infusions on Apr. 23, 1990. The dose of the formulation was gradually increased to 70 g IV daily. On Apr. 27, 1990, Antineoplaston AS2-1, 100 mg/ml infusions were added to the treatment and the dosage of this formulation was gradually increased to 20 g/24 h. The treatment was given in the form of continuous infusions through ambulatory pump. The complete evaluation performed on Jun. 22, 1990 revealed marked improvement in the patient's condition. The patient was feeling very well and did not have any complaints. The liver and spleen were no longer enlarged by physical examination. The laboratory tests on May 17, 1990 revealed T4 cell count of 82/mm$^3$. The repeated test on Jun. 4, 1990 revealed marked increase of T4 cell count to 133/mm$^3$. The increase of T4 cell count indicates improvement in the treatment of AIDS.

EXAMPLE 3

(Patient: RH)

The patient is a 32-year-old white male who was complaining of fever and night sweats. This patient was in good health until approximately 1985 when he was diagnosed as HIV positive. He did not use intravenous drugs, and most likely, his infection was due to homosexual contact. He did not have any treatment until Jun. 8, 1990 when he was started on zidovudine. Before beginning the treatment with Antineoplaston AS2-1, his T4 cell count was decreasing and T8 cell count was increasing.

The patient began treatment with Antineoplaston AS2-1, 500 mg capsules on Jun. 11, 1990. The patient was advised to take three capsules of Antineoplaston AS2-1 four times daily with meals. The treatment was tolerated very well without side effects. The most recent blood test of Jul. 30, 1990 revealed increase of T4 cell count and decrease of T8 cell count. Helper/suppressor ratio increased. His pre-treatment T4 cell count of Jun. 8, 1990 was 496/mm$^3$. Subsequent T4 cell counts were as follows: 484/mm$^3$ on Jul. 9, 1990 and 546/mm$^3$ on Jul. 30, 1990. Pre-treatment T8 cell count on Jun. 8, 1990 was 2232/mm$^3$. The following T8 cell counts were 1430/mm$^3$ on Jun. 9, 1990 and 1281/mm$^3$ on Jul. 30, 1990. T4/T8 ratio increased from initial 0.22 on Jun. 8, 1990 to 0.33 on Jul. 9, 1990 and 0.42 on Jul. 30, 1990.

EXAMPLE 4

(Patient: GD)

When coming under my care, the patient was a 34-year-old white female who was complaining of the presence of nodules in the genital area. The patient was in very good health until approximately 1980 when she was diagnosed with genital warts. Initially she did not receive any treatment, but when her disease progressed, she was started on Podophilin in 1979. She was taking such treatment on and off with chemical coagulation until 1986. The disease progressed further and between 1986 and 1988 she had a few electrical cauterizations. In January 1989, she had laser surgery, and in the first week of May 1990, she was again treated with Podophilin because of recurrence of the nodules. In spite of the treatment given, the disease was continually progressing.

Her initial pretreatment evaluation on Jun. 14, 1990 was significant for numerous nodules corresponding to genital warts in the genital area, covering the labia and reaching down to the anal area. The nodules were measured from 0.3 cm×0.3 cm diameter up to 1 cm×1.5 cm in diameter. They were movable and had pigmentation slightly darker than the skin. They were not painful to palpation.

The treatment with AS2-1 began on Jun. 14, 1990. The patient was advised to take four capsules qid with meals (149 mg/kg/24 h). On Jun. 20, 1990, alpha-Interferon 1.2 mlnU s.c. daily was added to the treatment program. The following day the dose of alpha-Interferon was increased to 1.5 mlnU s.c. daily. The patient decided to discontinue the treatment on her own on Jul. 20, 1990, but restarted again on Aug. 21, 1990 at the same dosage level. Such treatment was continued for approximately two weeks and discontinued again because the patient did not have enough money to purchase Interferon in the pharmacy.

When examined after the first week of treatment on Jun. 20, 1990, the patient was feeling generally well and her physical examination was significant for decrease of discoloration of the lesions in the genital area. Her physical examination on Aug. 21, 1990 revealed marked decrease of the size of the lesions, except for the one in the anal area.

EXAMPLE 5

(Patient: ND)

At the beginning of the treatment with AS2-1, the patient was a 42-year-old white female who was complaining of recurrent genital warts. The first eruption occurred in 1987, and initially, it was thought that the patient had Herpes infection. She was treated with oral Zovirax, but without any good effect. The biopsy confirmed changes consistent with human papilloma virus infection. Herpes culture was negative for Herpes simplex virus antigen. Zovirax was stopped in February 1990. Since then, the patient has been taking lysine 1000 mg daily, which was increased to 2000 mg daily one week before menstrual bleeding until the bleeding stopped.

The eruptions were covering both labia and made the patient very uncomfortable, so that it was even difficult for her to sit. They usually occurred from 4 to 6 weeks, and the worse eruption was usually noticed from 5 to 7 days before menstrual bleeding. She was told by her treating physician that there was no treatment available for her condition and that her genital warts may later progress into cancer. The pretreatment examination on Feb. 25, 1991 revealed fine nodularity seen on both labia.

The treatment with AS2-1 began on Feb. 25, 1991. The patient was advised to take four capsules qid with meals (150 mg/kg/24 h). On Feb. 24, 1991, alpha-Interferon 1.5 mlnU s.c. every other day (qod) was added to the treatment. After three days of treatment, the dose of alpha-Interferon was decreased to 0.6 mlnU s.c. qod, and on Mar. 4, 1991 increased again to 1.5 mlnU s.c. qod. On Jun. 3, 1991 after 98 days of treatment, the dose of alpha-Interferon was decreased to 1.5 mlnU every third day for five weeks, and then it was further decreased to every four days for another five weeks, and then alpha-Interferon was discontinued. However, the patient continued the treatment with AS2-1.

After 79 days of treatment on May 15, 1992, the patient was evaluated by her local gynecologist who found that her vaginal symptoms had dramatically improved. She has not had practically any complaints. Her physical examination revealed less erythromatous vaginal area. After application of acetic acid to the areas, which were biopsied before, there were no epithelial changes seen at that time. When examined on Jun. 3, 1991 after 98 days of treatment, the patient was feeling very well and did not report any complaints. She did not have any aggravation of the symptoms, which usually happened during menstrual bleeding. The physical examination was within normal limits, including the examination of the genitals. Fine nodularity seen on both labia were not evident at that time. The patient continued to do well after five months of treatment and did not have any evidence of recurrence of her disease. She stayed free from recurrence after approximately 10 months of treatment on Dec. 9, 1991.

Condylomata acuminata or genital warts are sexually transmitted disease. In 1968, virus particles have been identified in the cells of genital warts by electron microscopy (Dunn, A. E. G. et al., *Ultrastruct. Res.* 22:282 (1968)). It was proved further that genital warts are associated with Human Papilloma Virus (HPV) infection, in most cases, HPV6 and HPV11 (Gissmann, L. et al., *Int. J. Cancer* 29:143 (1982) and Gissmann, L. et al., *Proc. Natl. Acad. Sci.* U.S.A. 80:560 (1963)). The treatment with alpha-Interferon has been helpful in cases of genital warts, but it requires intralesional injections. Generally, treatment with systemic alpha-Interferon has not been effective (Condylomate International Collaborative Study Group, *JAMA* 265:2684 (1991)). The treatment of genital warts with Antineoplaston AS2-1 in conjunction with systemic (subcutaneous) low dose alpha-Interferon resulted in elimination and decrease of genital warts in two patients as described above.

EXAMPLE 6

(Patient: PG)

This patient came under my care on Jan. 21, 1986 for the treatment of Hodgkin's disease. At that time, she was a 26-year-old white female who was complaining of daily fever, perspiration, sore throat and numbness in toes of both feet. This patient was found to have in February 1985 a large mediastinal mass on the chest x-ray and involvement of hilar and paratracheal lymph nodes. The biopsy confirmed diagnosis of Hodgkin's lymphoma of mixed cellularity. She did well under the care of another physician, but finally developed progression of the disease.

At the beginning of the treatment under my care, the patient had a huge lobulated right anterior mediastinal mass extended from the level of thoracic inlet to the level of the diaphragm. She also had right paratracheal mass and possible involvement of mediastinal lymph nodes on the left side. Since Jan. 21, 1986, she has been receiving treatment with Antineoplaston AS2-1 and A10 capsules and Cytoxan tablets. Within the first two months of treatment, the patient went into remission but continued the treatment with A10 and AS2-1 until Sep. 27, 1991. From Aug. 9, 1988 through Oct. 4, 1988, she was also receiving chemotherapy with Velban and from May 14, 1990 until Dec. 28, 1990, she was taking low dose alpha-Interferon treatment.

It was found that during five years of treatment for Hodgkin's disease, the patient never developed any viral infection in spite of the fact that she was working with children who frequently suffered from viral infections. The patient was also taking chemotherapy with Cytoxan and Velban which would facilitate viral infection by decreasing body immunity. Before beginning the treatment with Antineoplaston AS2-1 and A10, the patient was usually having more than once a year such viral infection like influenza and common cold.

These six examples indicate the clinical activity of Antineoplaston AS2-1 against DNA viruses, for instance herpes and HPV, RNA viruses including retroviruses such as HIV, and RNA viruses which cause the common cold and flu, e.g., rhinoviruses, coronaviruses, orthomyxoviruses and paramyxoviruses.

What is claimed is:

1. A method of treating disease producing viral infections in an afflicted human host comprising:

administering to the host a pharmaceutical composition containing a therapeutically effective amount of a combination of compounds of the formula:

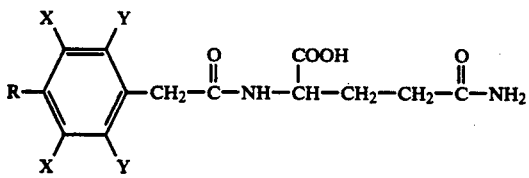  (A)

and

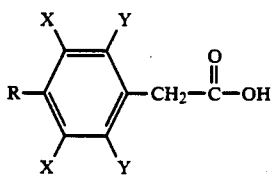  (B)

in a weight ratio ranging from about 1:1 to about 1:10 (A:B); wherein R is OH, $NH_2$, OW, or H; X is H, F, Cl, Br, I, OH, OW, $NO_2$, or $NH_2$; Y is H, F, Cl, Br, or I; W is

or a $C_1$ to $C_{12}$ aliphatic group;

Z is an aliphatic or aromatic group pf $C_1$ to $C_{12}$;

X and Y can both vary within the compound; or pharmaceutically acceptable salts thereof.

2. The method of claim 1 wherein the pharmaceutical composition contains a mixture of phenylacetylglutamine and phenylacetic acid or pharmaceutically acceptable salts thereof.

3. The method of claim 1 wherein the pharmaceutical composition contains a 1:4 ratio of A:B.

4. The method of claim 2 wherein the pharmaceutical composition contains a 1:4 ratio of phenylacetylglutamine sodium salt and phenylacetic acid sodium salt.

5. The method of claim 1 wherein the pharmaceutical composition is administered to humans in the amount of 0.5 to 60 g/day.

6. The method of claim 1 wherein the pharmaceutical composition is administered orally, topically or parenterally.

7. The method of claim 1 wherein the afflicted host is infected with herpes viruses.

8. The method of claim 1 wherein the afflicted host is infected with lentiviruses.

9. The method of claim 1 wherein the afflicted host is infected with adenoviruses.

10. The method of claim 1 wherein the afflicted host is infected with papovaviruses.

11. The method of claim 1 wherein the afflicted host is infected with rhinoviruses.

12. The method of claim 1 wherein the afflicted host is infected with coronaviruses.

13. The method of claim 1 wherein the afflicted host is infected with orthomyxoviruses.

14. The method of claim 1 wherein the afflicted host is infected with paramyxoviruses.

15. The method of claim 1 wherein the afflicted host is infected with retroviruses.

16. The method of claim 1 wherein the afflicted host is infected with human papilloma viruses.

17. The method of claim 1 wherein the afflicted host is infected with tumorogenic viruses.

18. The method of claim 1 wherein the pharmaceutical composition is administered systemically.

19. The method of claim 18 wherein the pharmaceutical composition is administered orally, parenterally, intravenously, intradermally, subcutaneously, or intraperitoneally.

* * * * *